United States Patent
Conway et al.

(10) Patent No.: US 7,562,583 B2
(45) Date of Patent: Jul. 21, 2009

(54) APPARATUS AND METHOD FOR MEASURING CRUSH-RESISTANCE OF GRANULAR MATERIALS

(75) Inventors: Michael W. Conway, Marlow, OK (US);
Ronnie L. Gregston, Marlow, OK (US);
Nick L. Moore, Marlow, OK (US);
Melissa Y. Walkingstick, Marlow, OK (US)

(73) Assignee: Stim-Lab, Inc., Duncan, OK (US)

( * ) Notice: Subject to any disclaimer, the term of this patent is extended or adjusted under 35 U.S.C. 154(b) by 535 days.

(21) Appl. No.: 11/499,930

(22) Filed: Aug. 7, 2006

(65) Prior Publication Data

US 2008/0060444 A1    Mar. 13, 2008

(51) Int. Cl.
*G01N 3/08* (2006.01)
(52) U.S. Cl. .......................... 73/821; 73/818
(58) Field of Classification Search ............ 73/818–825
See application file for complete search history.

(56) References Cited

U.S. PATENT DOCUMENTS

| | | | | |
|---|---|---|---|---|
| 4,581,253 A | * | 4/1986 | Evans et al. | 427/221 |
| 4,768,567 A | | 9/1988 | Travillian | |
| 4,848,145 A | * | 7/1989 | Blaschke et al. | 73/152.55 |
| 5,811,686 A | * | 9/1998 | Lavoie et al. | 73/821 |
| 6,109,486 A | * | 8/2000 | Lee et al. | 222/485 |
| 2005/0056428 A1 | * | 3/2005 | Jeffrey, Jr. | 166/308.1 |
| 2007/0225176 A1 | * | 9/2007 | Pope et al. | 507/221 |

OTHER PUBLICATIONS

"Recommended Practices for Testing Sand Used in Hydraulic Fracturing Operations", API Recommended Practice 56 (RP 56) First Ed. Mar. 1983.
Nader S. Rad and Mehmet T. Tumay, "Factors Affecting Sand Specimen Preparation by Raining", American Society for Testing and Materials, 1985, pp. 31-37.
Wijewickreme, Sriskandakumar and Byrne, "Cyclic loading response of loose air-pluviated Fraser River sand . . . ", NRC Canada, pp. 550-561.
J.C. Gottschling, "Analysis of Non-API Industrial Sands for Us ein Hydraulic Fracturing", SPE 98019, Copyright 2005, pp. 1-6.

* cited by examiner

*Primary Examiner*—Max Noori
(74) *Attorney, Agent, or Firm*—Claude E. Cooke, Jr.; Burleson Cooke L.L.P.

(57) ABSTRACT

Apparatus and method are provided for loading a cell for testing crush-resistance of a proppant or other granular material. The apparatus includes a rod valve and one or two screens selected to allow proppant to pluviate into the cell. Stress may be applied to the cell and the amount of proppant crushed by the stress may be measured. Measurements may be repeated to produce mean and variance values. Screen sizes may be varied to select sizes to minimize variance of measurements.

16 Claims, 9 Drawing Sheets

Fig. 1
(Prior Art)
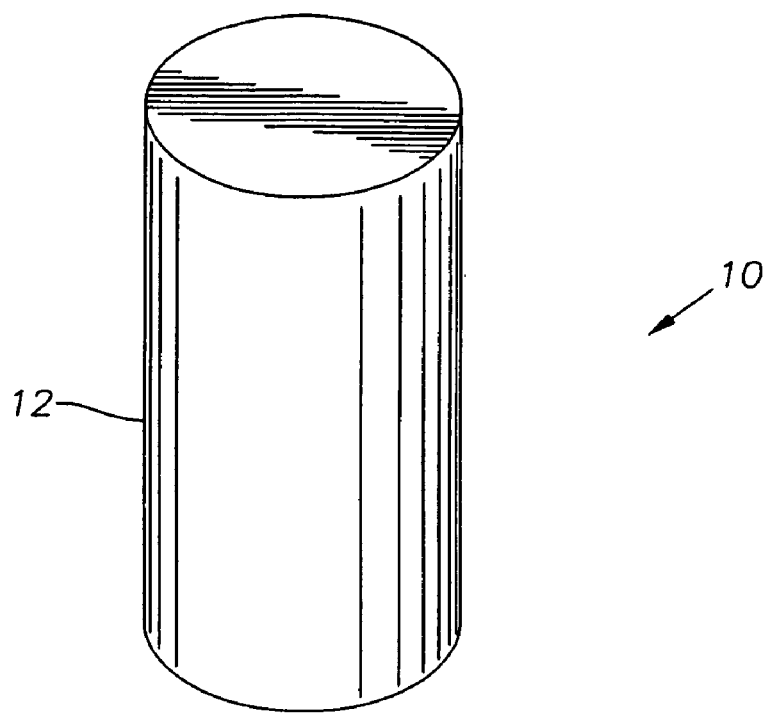
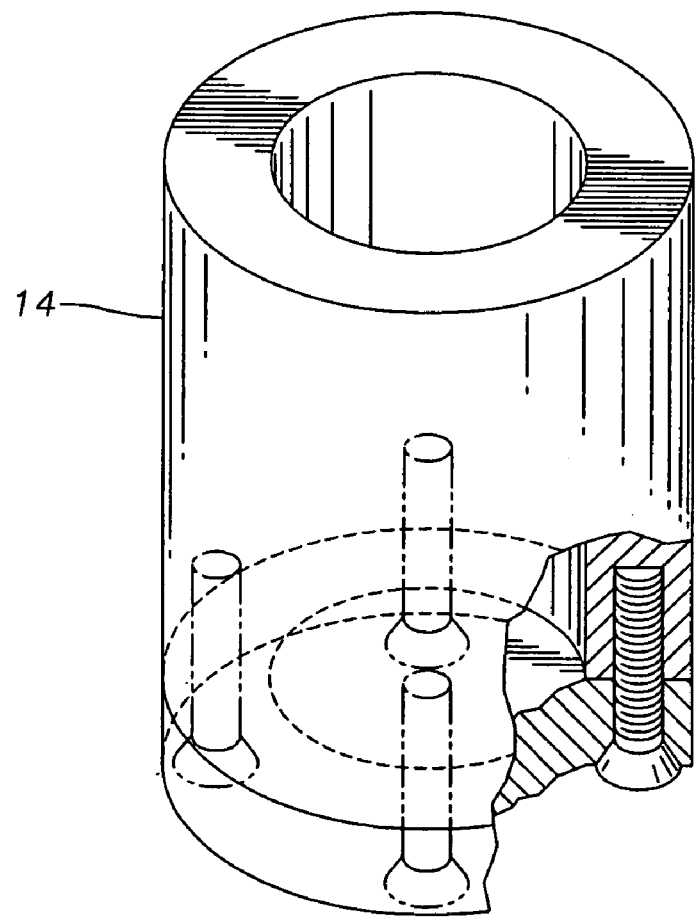

APPARATUS AND METHOD FOR MEASURING CRUSH-RESISTANCE OF GRANULAR MATERIALS

BACKGROUND OF THE INVENTION

1. Field of the Invention

This invention pertains to tests of granular materials. More particularly, apparatus and method are provided for testing crush-resistance of granular materials such as proppants used in wells.

2. Background of Inventions

Slurries of granular material are commonly pumped down oil and gas wells to improve the producing characteristics of the well. The most common procedure is to fracture the earth by pumping fluids at a high rate and then to pump a slurry of granular material down the well and into the open fracture. This process, called "hydraulic fracturing," may increase the production rate of wells up to several-fold. In another method to improve producing characteristics of a well, granular materials are packed around or in a wellbore to serve as a filter, in a process called "gravel packing." In both processes, the fluid in the slurry is separated from the granular material and the granular material is left in the well in the form of a packed bed.

In the hydraulic fracturing process, since the granular material is in a fracture in the earth, it is subjected to earth stresses, which may reach 10,000 psi or more. Stress tends to cause crushing of the material. The granular material used in the hydraulic fracturing process is called a "proppant" because it "props" the fracture to keep it open. Since the capacity for fluid flow through the proppant material is important and maximum flow capacity is needed to obtain maximum production rate from a well, it is important that crushing of proppants be measured.

Industry has long recognized the need for proppants that crush a minimum amount under stress. Silica sand was used almost exclusively as a proppant for many years and it was found to vary widely in composition and strength. A need arose for a test to compare the amount of crushing of different sands used as a proppant. In 1983, a committee organized by the American Petroleum Institute (API) published "Recommended Practices for Testing Sand Used in Hydraulic Fracturing Operations" (API Recommended Practice 56, March 1983). Section 8 of the document describes a "Recommended Frac Sand Crush Resistance Test." This test employs the cylindrical test cell shown in FIG. 1. The procedure includes sieving a sample of sand to the desired range of sizes and placing a measured amount of sand inside the cylinder to produce a sand concentration of 4 lbs per sq. ft. The API procedure states: "Pour the sand sample into the test cell constantly moving the source of the sand to keep the surface in the cell as level as possible." Then the procedure prescribes leveling the surface of the sand in the cell by inserting the piston in the cell and rotating the piston 180 degrees in one direction only without applying any force to the piston.

After the API cell is loaded with proppant, it is placed in a press and the force required to obtain a desired stress level in the cell is applied. The sample is then removed from the cell and sieved and the weight of crushed material passing through the smaller screen is measured and reported as a percentage of the weight of the original sample. The API committee recommended the maximum amount of fines for each mesh size range of sand that would be acceptable at stress levels such as 4,000 psi or 5,000 psi. For example, 20-40 mesh sand stressed to 4,000 psi was suggested to have maximum fines produced of 14%. Some natural sands that failed to pass the API crush test may have been rejected for use in hydraulic fracturing. This is illustrated for example in the paper SPE 98019, "Analysis of Non-API Industrial Sands for Use in Hydraulic Fracturing." It was reported that two samples of sand "failed the crush test which allows a maximum of 14% fines."

With the further development of synthetic or manmade proppants, the procedures developed for sand were also applied to compare these proppants. The technical groups comparing different natural and synthetic proppants have been limited by variability of results among different laboratories and by reproducibility of results within the same testing facility, particularly when tests are performed by different operators.

There is currently circulating an update of the API RP 56 reference in the form of document ISO TC 67/SC 3, dated Dec. 5, 2005. This document is not an international standard at this time; recipients of the document are invited to submit their comments. The proposed document contains the test and procedure utilizing the same cell as shown in FIG. 1 and a similar procedure for placing proppant in the cell. The amount of proppant to be used in the test is calculated from the "loose-pack" bulk density. "Crush stress level guidelines" are provided for manmade proppants and sand proppants, but no maximum amount of crushing is prescribed. The remark is added that: " . . . variance in crush results have been largely associated with the method of loading the crush cell."

U.S. Pat. No. 6,109,486 discloses a dry sand pluviation device. (The patent explains that the term "pluviation" is a term related to the Latin word for "rain" and refers to the fact that the granular particles fall like raindrops.) The pluviation device of the '486 patent is used to load test apparatus for soil mechanics studies. In the study of soil mechanics it is also important that the soil particles be placed in a uniform fashion that allows a precisely controlled and consistent soil layer density. The vessel of the invention is an open top box having vertical side walls and a horizontal bottom tray with multiple perforations uniformly spaced on a square or equilateral triangle pattern. The vessel has a moveable tray disposed below the stationary bottom of the vessel that has corresponding multiple perforations such that the slideable tray can be used to close the perforations in the bottom of the box.

U.S. Pat. No. 4,768,567 discloses a sand-filled apparatus for casting. Sand particles are placed within a foundry mold in preparation for casting by the lost foam process. A compressed air conduit is temporarily inserted to direct air flow toward the pattern and divert pluviating sand to promote even packing of the sand about the pattern.

In geotechnical testing, pluviation has been studied as a method to prepare reconstituted samples for testing. The effects of the structure of the "sand rainer" (the apparatus used to pluviate the sand into the testing apparatus) have been reported in "Factors Affecting Sand Specimen Preparation by Raining," *Geotechnical Testing J.*, Vol. 10, No. 1, Mar. 1987, pp. 31-37.

Soil mechanics properties such as the cyclic loading response of sand have been observed to be dependant on the method of formation of the specimens for testing. ("Cyclic loading response of loose air-pluviated Fraser River sand for validation of numerical models simulating centrifuge tests," *Can. Geotech. J.*, 42 550-561 (2005) Air-pluviated specimens were more susceptible to liquefaction under cyclic loading than water-pluviated samples. Differences between the two specimens were attributed to differences in particle structure; the differences highlighted the importance of "fabric effects" in the assessment of mechanical response of sands. A simple "raining technique" that allowed relatively independent control of both fall height and mass flow rate of sand was found to be preferable for the preparation of specimens. It was found that the as-placed density of the river sand increased with increasing fall height and decreasing mass flow rate. Sand was rained through a 1 millimeter sieve or a 2.5 millimeter sieve. The effects of flow rate and average fall height on the relative density of packs of the river sand was provided.

Alternative granular materials available in industry for use in hydraulic fracturing now include silicon sand, resin coated sand and a variety of ceramic granular materials, which may also be resin-coated. The crush test originally proposed in the API RP 56 has been used many thousands of times to compare the strength of these various granular materials. It has been found that crush-resistance tests by different laboratories (sometimes called "round-robin tests") vary over a broader range than is desirable to make reliable comparisons of different materials. Crush-resistance tests are also used for quality control during manufacture of manmade proppants, where variations in test results may cause difficulties in manufacturing process optimization. It is believed that the principal cause of the variations in crush results is the difference in loading procedure between different operators and different laboratories. The present procedures require that a part of the procedure that can have a significant effect on crush results be carried out by a person. Therefore, what is needed is a crush-resistance test for granular materials to compare the crush-resistance of various materials that produces results independent of the operator of the tests.

SUMMARY OF THE INVENTION

Apparatus and method are provided for measuring the crush-resistance of granular materials without operator influence on results. A modified test cell allows for measuring the porosity of a sample after it has been placed in the cell. Apparatus and method for air-pluviating a sample into the test cell at a selected range of rates and from a selected fall distance to produce a uniform sample are provided.

BRIEF DESCRIPTION OF THE DRAWINGS

FIG. 1 is an isometric drawing of the test cell prescribed in an API procedure (Prior Art).

DETAILED DESCRIPTION

Figure 2:
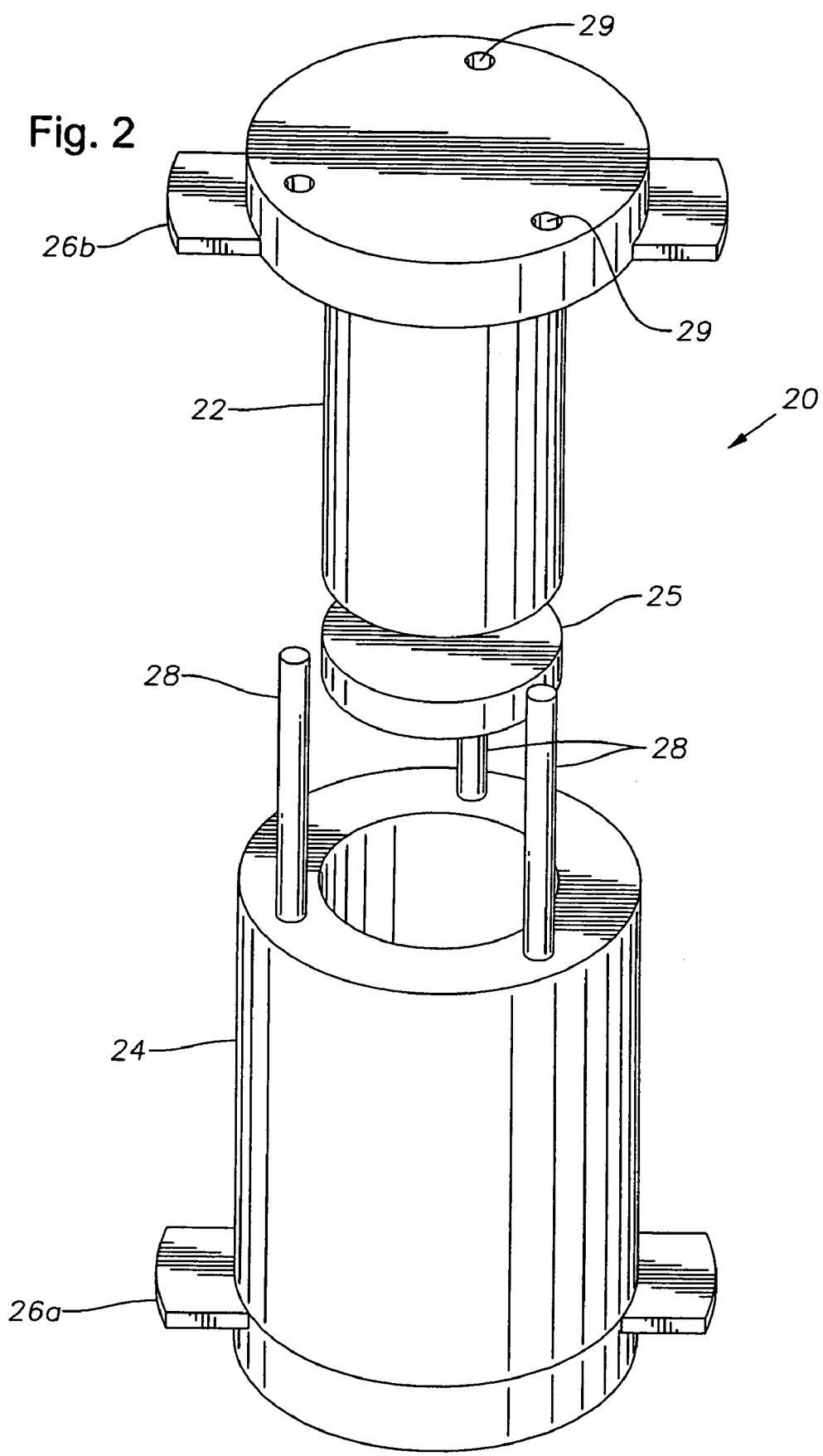
FIG. 2 is an isometric drawing of the test cell disclosed herein.

FIG. 1 shows prior art apparatus 10 used for measuring crush of proppants. The apparatus consists of cylinder 12 which is adapted for a close fit inside cup 14. A selected amount of proppant that has been sieved to a selected size range (such as 20-40 mesh) is poured into cup 14, cylinder 12 is then inserted and rotated 180 degrees for leveling the proppant and the apparatus is then placed between the platens of a press. Stress is applied to a selected level, the apparatus is removed from the press and the proppant sample is emptied upon a screen or set of screens. The amount of proppant crushed such that it will pass through the smallest screen used to sieve the proppant is reported as a percentage of the sample that is crushed by the applied stress. This is the apparatus described in API RP56, FIG. 8.1. The diameter of the piston is usually 2 inches.

Referring to FIG. 2, test cell 20 disclosed herein is shown. Cell 20 includes piston 22 and cup 24, which may be sized the same as the apparatus shown in FIG. 1. Spacer piece 25, used to avoid excessive wear on the bottom of cup 24 during tests, is sized to fit in cup 24 also. Tabs 26a and 26b are a measurable distance apart when piston 22 and disk 25 are tightly fit to the bottom of cup 24. Therefore, tabs 26a and 26b may be used for measuring the height of a proppant bed in cup 24. Proppant bed height, along with cell diameter and proppant density, can be used to calculate proppant porosity. Rods 28, adapted to be placed in holes 29, are used for aligning and maintaining the alignment of piston 22 in cup 24.

Figure 3:
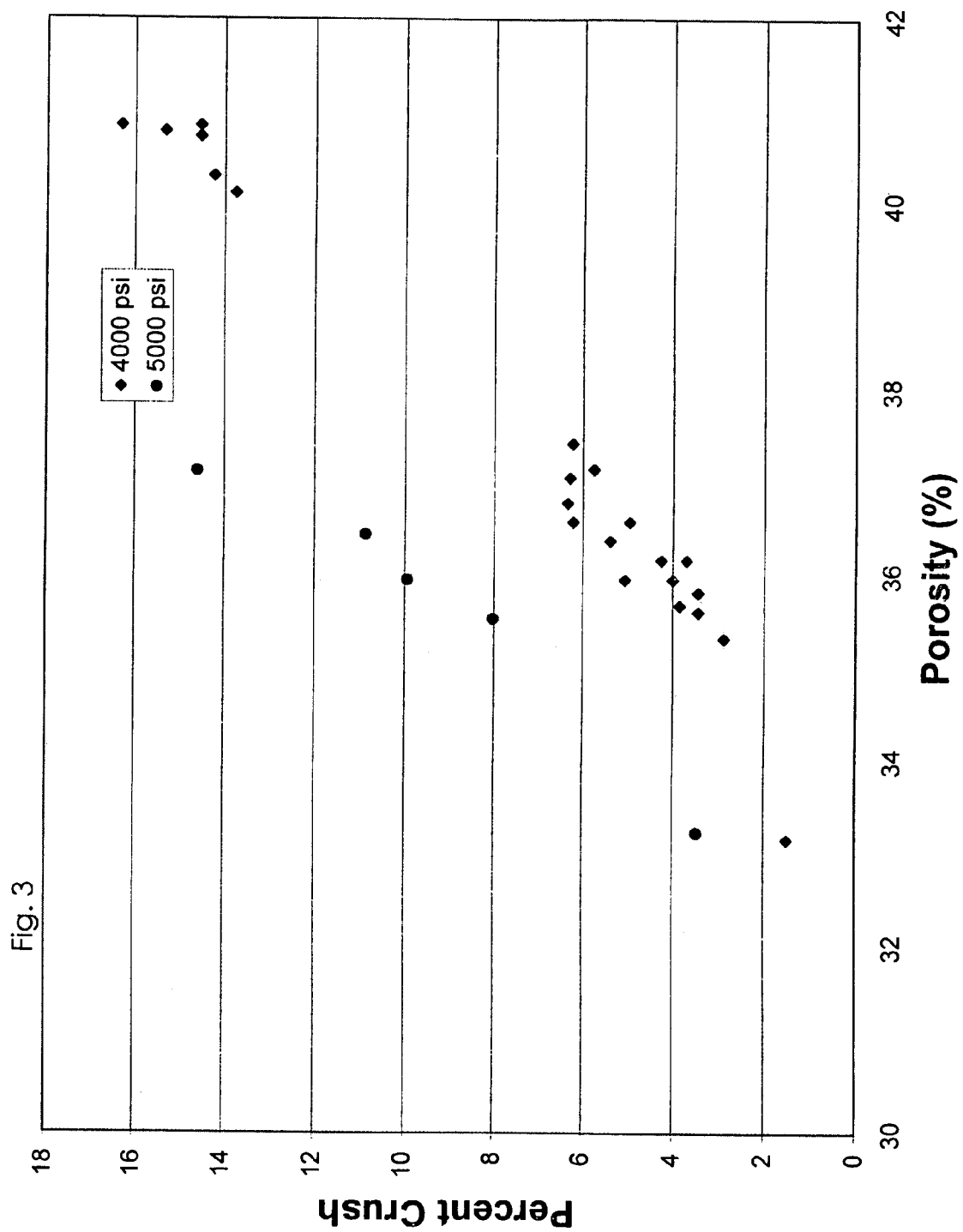
FIG. 3 is a graph of the effect of porosity on the crush of sand.

Using apparatus 20 to measure the percent crush and porosity of Brady sand having a mesh size of 20-40 resulted in the data shown in FIG. 3. These data are for stress levels of 4,000 psi or 5,000 psi after the sand was placed in the cell using different procedures. The data readily show that crush of sand is increased at both stress levels as porosity of the sample (measured at 200 lb force in apparatus 20) increased. These data illustrate the need for forming a proppant bed having a more uniform porosity within apparatus 20 in order to obtain crush results that are indicative of the strength of the material being tested.

Figure 3A:
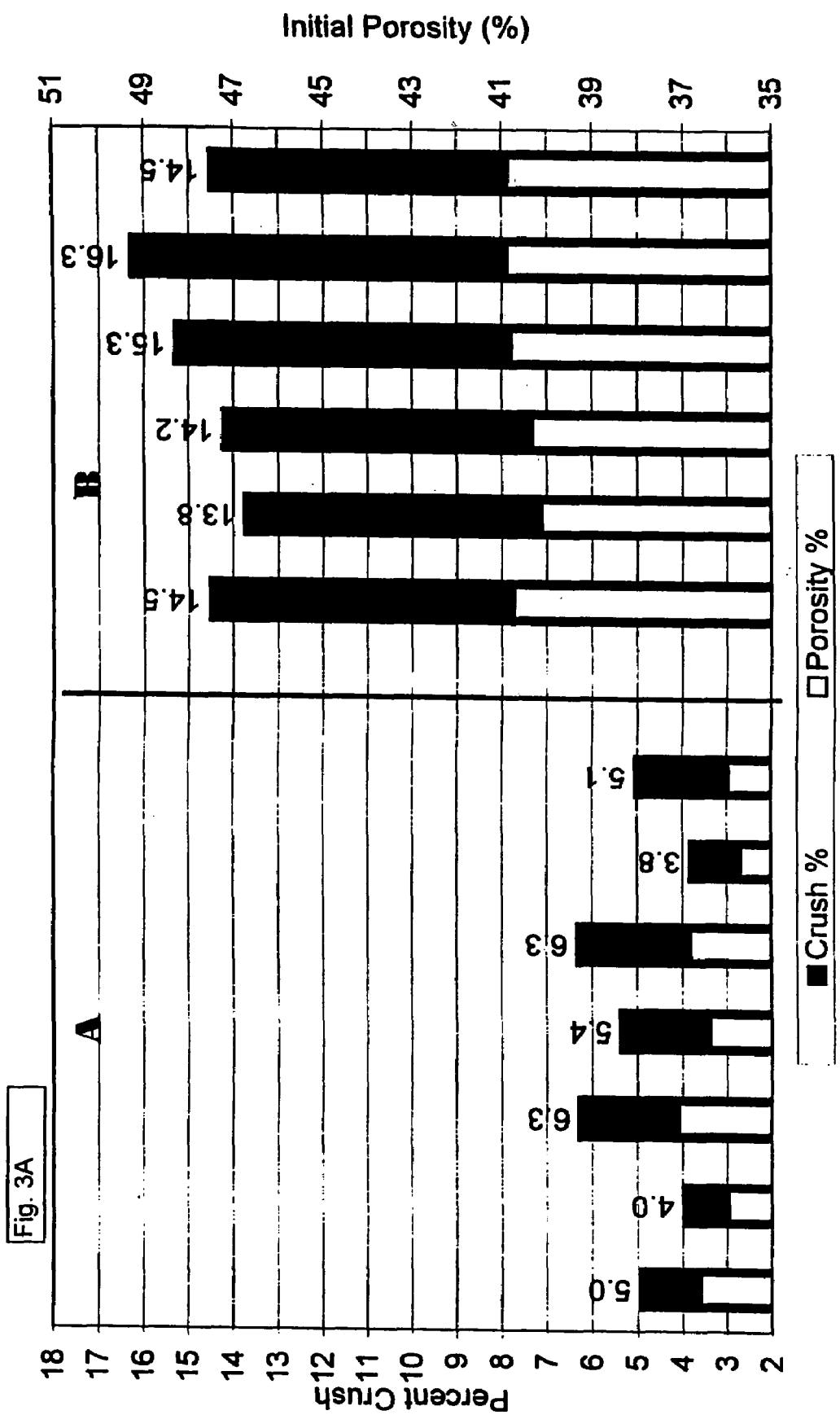
FIG. 3A is a chart of porosity and percent crush of 20-40 mesh sand for samples that produced a part of the data shown in FIG. 3.

FIG. 3A shows results of crush tests for 20-40 Brady sand at 4000 psi stress. The data shown in Section A of the chart were obtained by loading the sand samples using the API crust test procedure described above. Data in Section B were obtained by loading the sand using the ISO procedure used for loading the bulk density cell, which involves releasing the sand through a funnel into the test cell. Both procedures produced results that are somewhat consistent, but which varied widely.

Other experiments show that even if porosity is maintained in a limited range, results of crush tests still exhibit more variation and lack of reproducibility than desired. Furthermore, the data indicate that control of porosity alone is not adequate to minimize variations in results. Porosity may be decreased for example by vibrating apparatus 20 with a proppant sample within. After control of porosity, further steps were found to be needed to improve reproducibility of results and make results operator-independent. Also, it is difficult to standardize vibration as a method of obtaining uniform porosity and vibration of a proppant bed causes rearrangement of particles and size segregation that can have an effect on crush tests.

Figure 4:
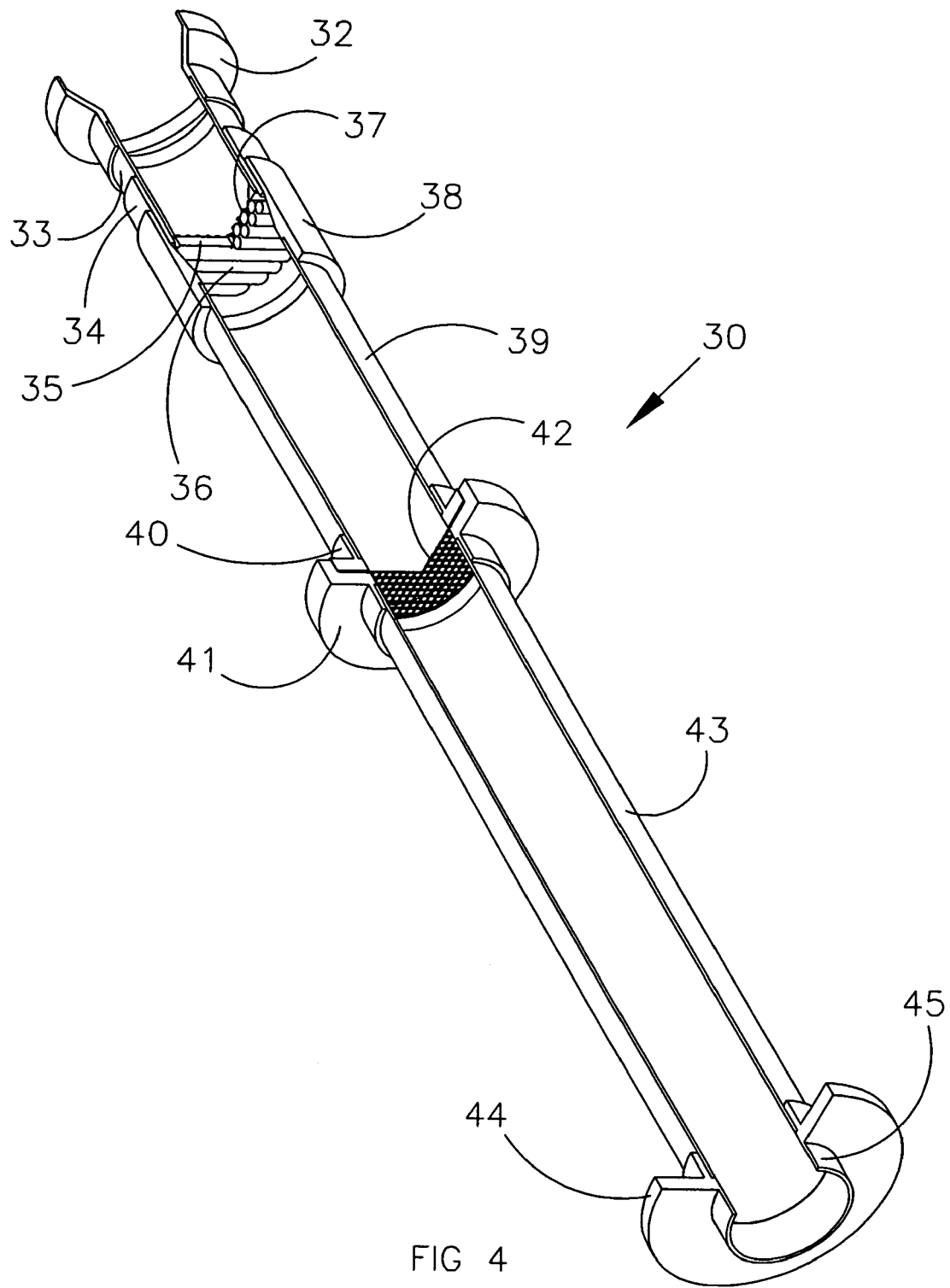
FIG. 4 is an isometric partial section from below of an air-pluviation device disclosed herein.
Figure 5:
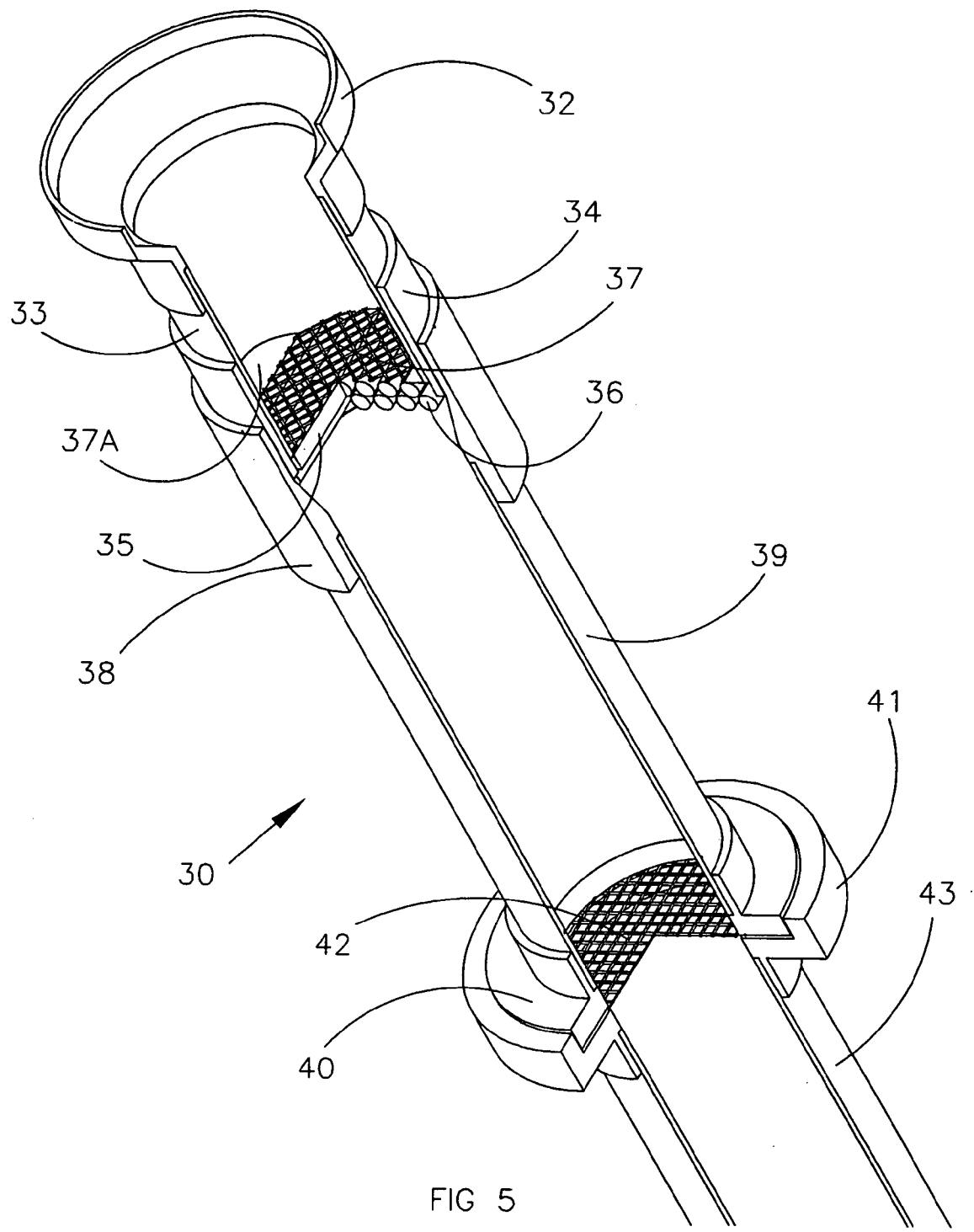
FIG. 5 is an isometric partial section of the top portion of the device of FIG. 4 from above.

The realization that controlling porosity alone is not sufficient, and the need for equipment that can be operated without requiring steps that may vary with the operator, led to the development of long-tube loading device 30 shown in FIGS. 4 and 5. Referring to FIG. 4, which is a view from below, funnel 32 is a receiver for granular material to be tested. It is attached to inside sliding cylinder 33, which is sized to slide inside cylinder 34. Top row of rods 35 is fixed in cylinder 33 and bottom row of rods 36 is fixed in cylinder 34. The two rows of rods form a valve for the granular material to be tested. Size and spacing of rods in each row is selected to allow proppant that is to be tested to pass through gaps between rods when the rows are separated by moving cylinder 33 upwards. Preferred sizes of the rods are provided in Table I. A preferred diameter of the rods for most proppant sizes is 0.125 inch. The center-to-center distance between rods of this size is preferably in the range from about 0.240 to 0.245 inch, which leaves a gap for the rod that must interface into it from about 0.005 to 0.010 smaller than the rod diameter. For other rod sizes, a gap from about 0.005 to 0.010 inch smaller than the rod diameter is preferred. When rows of rods 35 and 36 are placed in contact by lowering cylinder 33 to a resting position, proppant to be tested is held above the rod valve. Upper screen 37 may be placed on top row of rods 35.

Collar 38 (FIG. 4) is attached to upper tube section 39, which may have a length of 7 inches and is designed to conduct proppant to lower screen 42. The length of this section is not believed to be critical, but it should be long enough to allow the falling proppant to gain momentum. Upper collar 40 and lower collar 41 are designed to join upper tube section 39 and lower tube section 43, with lower screen 42 fixed therebetween. Collars 40 and 41 may be held together mechanically by screws, clamps or any fastening mechanism. Common C-clamps are adequate. The mesh size of lower screen 42 is selected to allow granular material to pass through lower screen 42 at a rate that leads to obtaining uniform deposition of proppant below. Preferred screen openings sizes of lower screen 42 for different mesh sizes of granular material change according to the grain size that is to be tested. Lower section 43 is selected to provide a drop height to decrease porosity of the proppant bed that comes to rest in a test cell below. A preferred length of section 43 is about 12 inches. Attached to the bottom of section 43 is flange 44 and guide 45. Guide 45 is designed to have an outside dimension equal to the inside dimension of a test cell to be loaded with granular material, such as cell 20 in FIG. 2. The inside diameter of cell 20 is commonly 2 inches, so the inside diameter of the flow channel below the valve formed by rows of rods 35 and 36 is two inches less twice the thickness of guide 45. Preferably, guide 45 is thin-walled. The bore is made such that it is continuous through device 30 when the parts are assembled. The material used for construction of device 30 is preferably mild steel. Erosion makes aluminum a poor choice and plastic allows build-up of static electricity, which can modify the pluviation process.

FIG. 5 shows device 30 from above. This view allows upper screen 37 to be illustrated, along with insert 37A, which may be present on each side of screen 37 to guide granular material through screen 37. Screen 37 is preferably oriented such that the wire mesh is at an angle of 45 degrees with respect to rods 35 and 36. The screens may be those commonly used for sieving granular materials.

While the bore of device is illustrated as a cylinder, it should be understood that a bore of any cross-sectional shape may be used, so long as the cross-section is the same from cup 32 through guide 45. For example, a device having an elongated cross-section of the bore shaped to provide granular material to a fracture conductivity cell may be used.

For loading of a test cell with proppant, device 30 is placed with the bore exactly aligned with the bore of cup 24 (FIG. 2). A level is preferably used to ensure that device 30 is in a vertical position when proppant is air-pluviated into a device such as device 20.

The procedure for pluviating a granular material for measuring crush-resistance is as follows:

assemble device 30 of FIG. 4, using selected sizes of rods 35 and 36 and selected spacing of the rods and selected opening sizes of screens 37 and 42;

place the test cell that is to be loaded with granular material on a level surface and place guide 45 in the test cell;

check that device 30 is vertical;

place the sample to be tested into the top of the device with the rod valve formed by rod layers 35 and 36 in contact so the valve is closed;

lift cup 32 so as to open the valve. The drop rate of the proppant is controlled by the combination of the screen sizes and the rod size relative to the size of the granular material.

Figure 6:
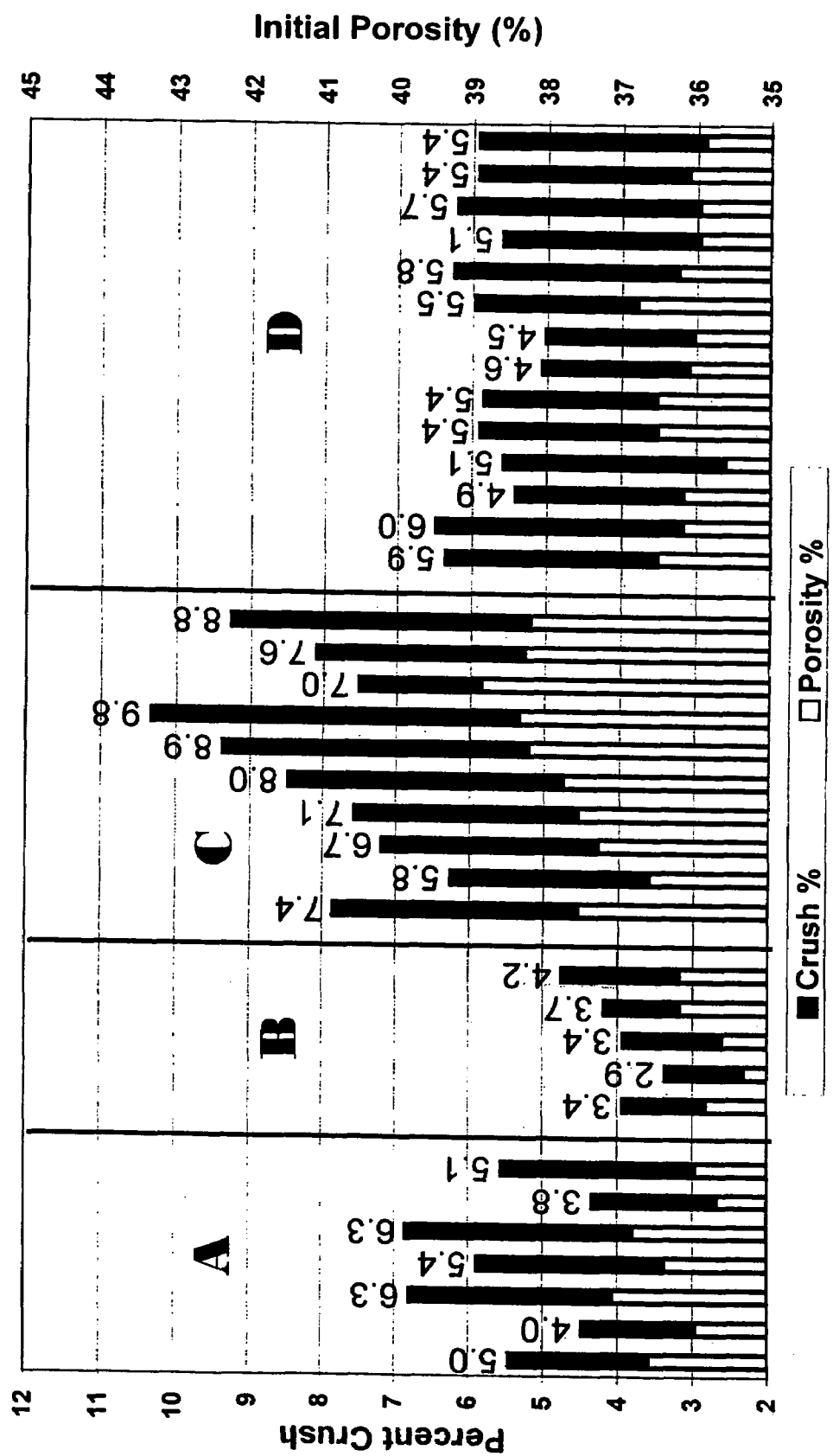
FIG. 6 is a chart of porosity and percent crushing of 20-40 mesh sand for different loading methods.

FIG. 6 shows results of crush tests with different methods used for loading proppant into the modified prior art API test cell (FIG. 2). The proppant samples were 20-40 mesh Brady sand provided by Oglebay Norton. The data shown are porosity at a stress level of 200 psi and percent crush at 4000 psi. Percent crush was measured by the procedure described above and in API RP56. Porosity is defined as the void space in a proppant bed divided by the total volume. It is calculated using well known methods. The height of the bed was determined by measuring the distance between tabs 26a and 26b (FIG. 2) with a telescoping gauge and a micrometer. The porosity shown was measured at a force of 200 lb on the piston, which is 63 psi. The amount of sand used in each crush test was 39.55 grams.

The first section of data (indicated by "A") in FIG. 6 results from measurements after the sand was loaded according to the procedure outlined in API RP 56. Sand was poured into the test cell while making an effort to distribute it evenly in the cell. The piston was inserted and rotated 180 degrees. Of seven measurements, porosity varied from 35.7 percent to 37.1 percent with a mean value of 36.34 and a standard deviation of 0.5 percent Crush percent varied from 3.8 to 6.3 percent with a mean value of 5.13 percent and a standard deviation of 0.99 percent.

The second section of data (indicated by "B") in FIG. 6 results from measurements made by pouring proppant into the cell and then leveling the top of the proppant bed with a horizontal blade attached to a handle such that the blade could be lowered and rotated to level the proppant. The piston was then inserted and rotated 180 degrees. Of five measurements, porosity varied from 35.3 percent to 36.2 percent with a mean value of 35.81 percent and a standard deviation of 0.37 percent. Crush varied from 2.9 percent to 4.2 percent with a mean value of 3.54 percent and a standard deviation of 0.49 percent.

The third section of data (indicated by "C") in FIG. 6 results from measurements made by using the long tube loading device of FIG. 4 without screen 37 but including screen 42. Screen 42 was 8 mesh. Rod diameter in the rod rows 35 and 36 was 0.125 inch. Proppant was poured into cup 32, then cup 32 was raised to open the valve. Sand fell through the device and into a test cell rapidly. Of ten measurements, porosity varied from 36.6 to 38.8 with a mean value of 37.85 percent and a standard deviation of 0.65 percent and crush varied from 5.8 to 9.8 percent with a mean value of 7.7 percent and a standard deviation of 1.20 percent.

Finally, in the fourth section of data (indicated by "D") in FIG. 6, results from measurements made by using the long tube loading device of FIG. 4 as shown in the figure, with both Screens 37 and 42 present. The screens were both 8 Mesh. Of fourteen measurements, porosity varied from 35.6 to 36.8 with a mean of 36.18 percent and a standard deviation of 0.31 percent. Crush varied from 4.5 percent to 6.0 percent with a mean of 5.34 percent and a standard deviation of 0.45 percent. These data show the effect of screen 37 in lowering the variance of measurements. A lower variance in results allows more definitive comparison of proppants.

Figure 7:
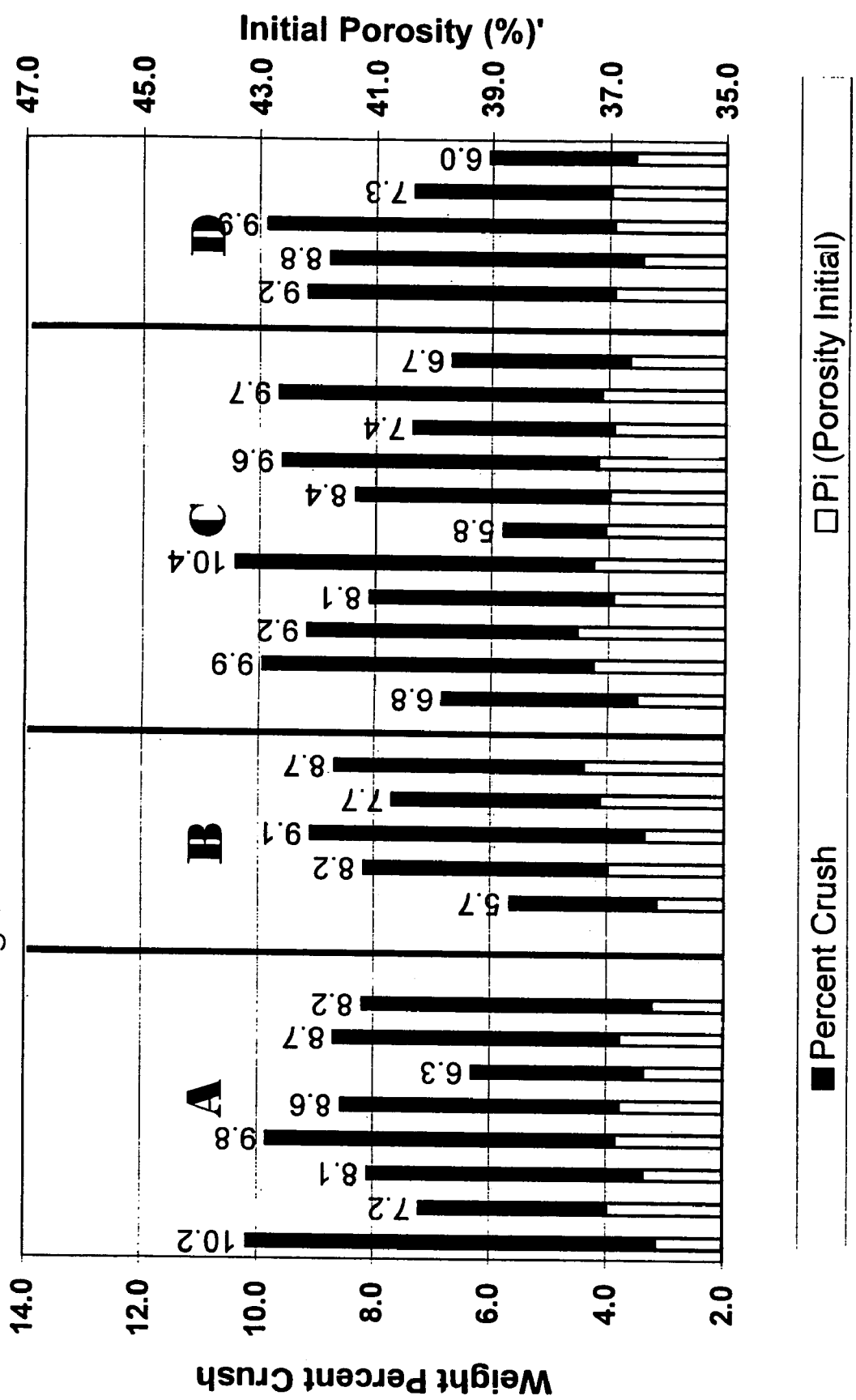
FIG. 7 is a chart of porosity and percent crushing of 12-20 mesh sand.

FIG. 7 shows results of crush tests with different methods used for loading proppant into the test cell disclosed in this application (FIG. 2). The proppant samples were 12-20 mesh Brady sand provided by Vulcan Chemicals. Measurements were made at a stress level of 3000 psi. The data shown are percent crush and porosity determined in the manner described for FIG. 6. The first section of data (indicated by "A") in FIG. 7 results from measurements after the sand was loaded according to the procedure outlined in API RP 56. Of eight measurements, porosity varied from 36.1 percent to 37.0 percent with a mean value of 36.55 and a standard deviation of 0.32 percent. Crush percent varied from 6.3 to 10.2 percent with a mean value of 8.38 percent and a standard deviation of 1.27 percent.

The second section of data (indicated by "B") in FIG. 7 results from measurements made by using the long tube loading device of FIG. 4 without screen 37 but including screen 42. Screen 42 was 5 mesh. Rod sizes in the valve were 0.125-inch. Of five measurements, porosity varied from 36.1 to 37.4 with a mean value of 36.80 percent and a standard deviation of 0.53 percent and crush varied from 5.66 to 9.1 with a mean value of 7.86 percent and a standard deviation of 1.34 percent.

The third section of data (indicated by "C") in FIG. 7 results from measurements made by using the long tube loading device of FIG. 4 without screen 37 but including screen 42. Screen 42 was 8 mesh. Rods in the rod sections in the valve were 0.125-inch diameter. Of eleven measurements, porosity varied from 36.5 to 37.5 with a mean value of 37.03 percent and a standard deviation of 0.29 percent and crush varied from 5.79 to 10.4 with a mean value of 8.36 percent and a standard deviation of 1.53 percent.

The fourth section of data (indicated by "D") in FIG. 7 results from measurements made by using the long tube loading device of FIG. 4 without screen 37 but including screen 42. Screen 42 was 8 mesh. Rod diameters in the valve were 0.125-inch. After pouring proppant into the device, the top of the proppant bed was leveled with a horizontal blade attached to a handle such that the blade could be lowered and rotated to level the proppant before opening the valve to load the crush cell. Of five measurements, porosity varied from 36.4 to 37.0 with a mean value of 36.76 percent and a standard deviation of 0.25 percent and crush varied from 6.05 to 9.9 with a mean value of 8.24 percent and a standard deviation of 1.53 percent. These results show that leveling of the proppant on the valve does not improve the variance in crush results, which is larger than desired for all the loading procedures. The only step under direct operator control is the step of leveling the proppant, and it did not affect the variance in results, which indicates that the device provides operator-independent results.

Figure 8:
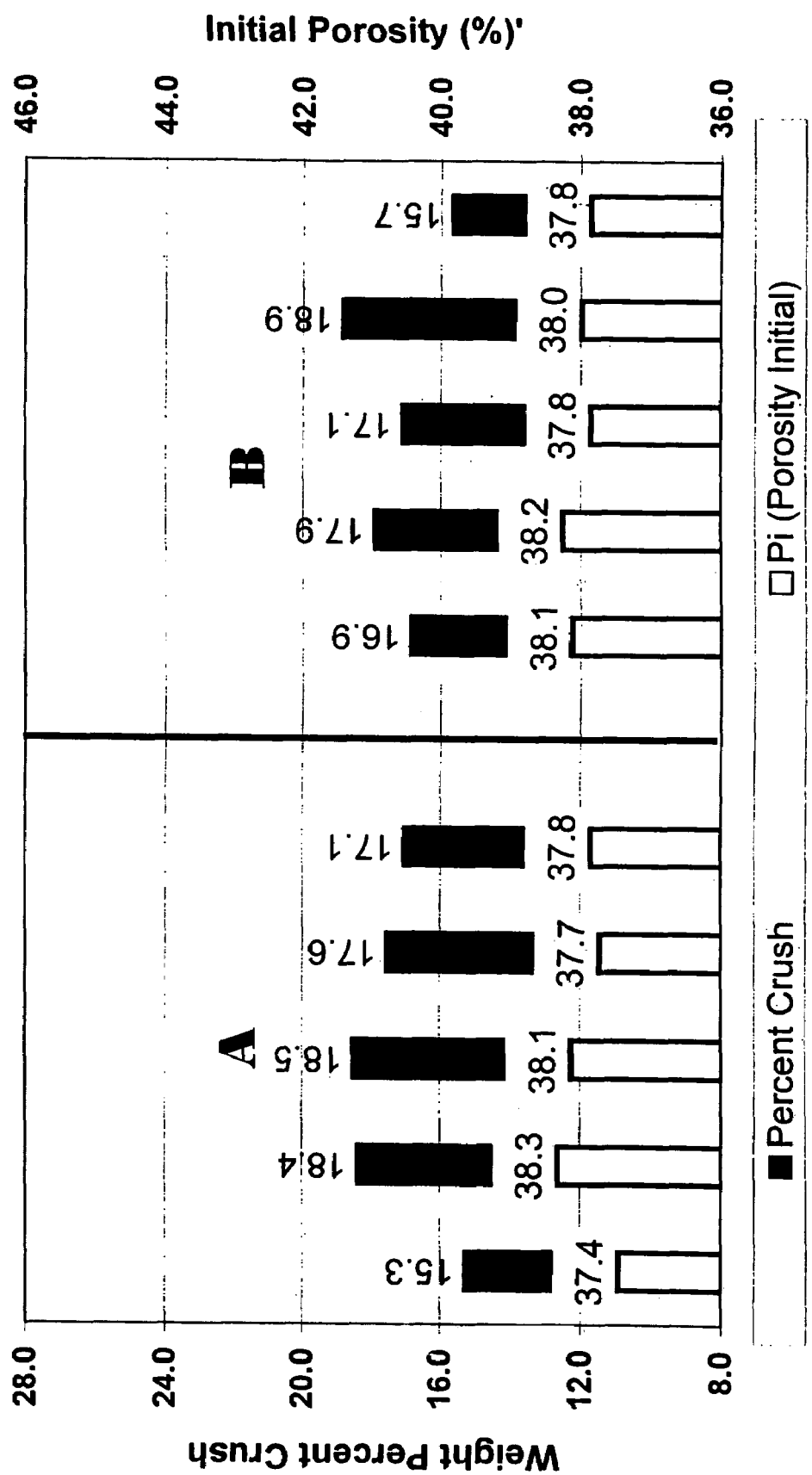
FIG. 8 is a chart of porosity and percent crushing of 8-16 mesh sand.

FIG. 8 shows results of crush tests with different methods used for loading proppant into the test cell disclosed in this application (FIG. 2). The proppant samples were 8-16 mesh Brady sand provided by Vulcan Chemicals. Measurements were made at a stress level of 3000 psi. The data show percent crush and porosity determined in the manner described for FIG. 6. The first section of data (indicated by "A") in FIG. 8 results from measurements after the sand was loaded according to the procedure outlined in API RP 56. Of five measurements, porosity varied from 37.4 percent to 38.3 percent with a mean value of 37.87 percent and a standard deviation of 0.33 percent. Crush percent varied from 15.3 to 18.5 percent with a mean value of 17.38 percent and a standard deviation of 1.30 percent.

The second section of data (indicated by "B") in FIG. 7 results from measurements made by using the long tube loading device of FIG. 4 without screen 37 but including screen 42. Screen 42 was 5 mesh. Rod diameters in the valve were 0.1875-inch. Of five measurements, porosity varied from 37.8 to 38.2 with a mean value of 38.0 percent and a standard deviation of 0.17 percent and crush varied from 15.7 to 18.9 with a mean value of 17.31 percent and a standard deviation of 1.19 percent. Larger rods and rod spacing were necessary with the larger proppant size.

The screen sizes and rod diameters and spacings of the long tube loading device disclosed herein must be adjusted for use with different proppant sizes. Suitable screens and spacings are selected from those that allow the proppant to pass through due to gravity. For example, a rod spacing of 0.125 inch will pass proppant sizes up to and including 12-mesh proppant mixtures. The upper screen must be large enough to prevent the screen being 'blinded" by the proppant lying stationary on the screen. It was found that proppant placed statically on top of a screen will form aggregates of up to 3 proppant grains, which may "blind" the screen. Dilute particles with momentum will easily pass a much smaller screen, with opening sizes approaching the diameter of the individual particles. Openings in the top screen will be as large as or larger than the openings in the screen used in the lower section. External vibrations which provide momentum to disrupt aggregates are not required using the disclosed device according to the preferred screen sizes and valve rod diameters listed in Table I. The lack of required vibrations and the fact that the operator has no control over how a sample pluviates into a test cell allows the device disclosed herein to produce results that are operator-independent. This was confirmed by repeated tests of the same proppant by different operators, which produced results of mean crush percentage that were independent of operator when the apparatus included the preferred screen sizes and valve rod sizes listed in Table I. The apparatus and methods disclosed herein allow different groups to produce well-defined data on crushing of granular materials.

TABLE I

Preferred Screen Sizes and Valve Rod Sizes

| Proppant mesh size to be pluviated | Screen mesh | | Rod Spacing (inch) |
|---|---|---|---|
| | Upper | Lower | |
| 40-60 | 20 | 22 | 0.125 |
| 30-70 | 14 | 18 | 0.125 |
| 30-50 | 14 | 18 | 0.125 |
| 20-40 | 8 | 8 | 0.125 |
| 16-30 | 6 | 8 | 0.125 |
| 12-20 | none | 8 | 0.125 |
| 8-16 | none | 5 | 0.1875 |

A range of screen sizes may be used near the preferred sizes, but results must be compared to determine that structure of the pluviated proppant bed has not been changed to produce different results. An operator may adjust both screen sizes, perform a series of crush tests, and arrive at screen sizes that produce the most reproducible results for a given proppant or other granular material.

Data presented here were obtained using the test cell of FIG. 2, which includes a cylinder having a diameter of 2 inches. It should be understood that the methods and apparatus disclosed here can be used in proppant-testing cells having other shapes and sizes. For each shape and size, the pluviating device may be formed having the shape and size of the test cell. For example, a conductivity test cell used for measuring fluid conductivity of a layer of proppant under stress, which may have dimensions of a proppant layer 1.5 inches wide and 5.5 inches long, for example, may be loaded by a pluviator constructed and operated according to the apparatus and methods disclosed herein.

Although the present disclosure has been described in detail, it should be understood that various changes, substitutions and alterations can be made thereto without departing from the scope and spirit of the invention as defined by the appended claims.

What we claim is:

1. Apparatus for loading a proppant into a test cell for measuring strength of the proppant, comprising:
    a valve section including two layers of spaced rods having selected diameters for holding proppant when in a closed position and allowing flow of proppant through the valve section when in an open position, the valve section having an inlet and a channel therethrough;
    an upper tube section attached to the valve section at an upper end of the upper tube section and having a channel adapted to be continuous with the channel through the valve section;
    a lower tube section adapted to be attached to the lower end of the upper tube section and having a channel adapted to be continuous with the channel through the upper tube section and a guide on the lower end thereof, the guide being adapted to guide proppant to the test cell; and
    a screen disposed between the upper tube section and the lower tube section.

2. The apparatus of claim 1 further comprising a screen disposed in the channel through the valve section.

3. The apparatus of claim 1 wherein a screen opening size of the screen disposed between the upper tube section and the lower tube section is selected according to the size of the proppant.

4. The apparatus of claim 1 wherein the selected diameter of the rods is in the range from about 0.125 inch to about 0.1875 inch.

5. The apparatus of claim 1 wherein the channel through the valve section, the upper tube section and the lower tube section has a circular shape.

6. The apparatus of claim 1 wherein the channel through the valve section, the upper tube section and the lower tube section has a shape that is selected to adapt to a conductivity test cell.

7. A method for loading a proppant into a test cell for testing crush of the proppant under stress, comprising:
    selecting a screen size and a valve rod size of a valve according to the size of the proppant and assembling the apparatus of claim 1 and placing it in a vertical position;
    placing the test cell below the apparatus;
    adding a selected amount of proppant in the valve section of the apparatus;
    opening the valve in the valve section and collecting the proppant in the test cell.

8. The method of claim 7 wherein the step of selecting a screen size and a valve rod size according to the size of the proppant includes selecting the values of Table I.

9. The method of claim 7 wherein the step of selecting a screen size and valve rod size according to the size of the proppant includes varying the screen size and measuring an effect on variance of results of crush testing.

10. A method for testing crush-resistance of a granular material, comprising:
    selecting a screen size and a valve rod size of a valve according to the size of the granular material and assembling the apparatus of claim 1 and placing it in a vertical position;
    placing a test cell below the apparatus;
    adding a selected amount of granular material above the valve;
    opening the valve and collecting the granular material in the test cell;
    applying a selected stress to the test cell; and
    removing the granular material from the test cell, measuring the amount of crushed material and calculating the percentage of crushed material as a percentage of the selected amount of granular material above the valve.

11. The method of claim 10 further comprising repeating the steps of claim 10 a selected number of times and calculating a mean value of the percentage of crushed material.

12. The method of claim 10 further comprising repeating the steps of claim 10 a selected number of times and calculating a variance of the percentage of crushed material.

13. The method of claim 12 further comprising selecting a different value of screen size and repeating the steps of calculating the variance for the different value of screen size.

14. The method of claim 13 further comprising selecting the value of screen size that produces a minimum value of the variance.

15. The method of claim 7 further comprising adding a screen in the channel through the valve section before opening the valve in the valve section and collecting the proppant in the test cell.

16. The method of claim 10 further comprising adding a screen in the channel through the valve section before opening the valve in the valve section and collecting the proppant in the test cell.

* * * * *